(12) United States Patent
Lin

(10) Patent No.: US 7,406,186 B2
(45) Date of Patent: Jul. 29, 2008

(54) DERMATOGLYPH TEST SYSTEM

(76) Inventor: Ruei-Bin Lin, P.O. Box 36-80, Tai-Chung City (TW)

( * ) Notice: Subject to any disclaimer, the term of this patent is extended or adjusted under 35 U.S.C. 154(b) by 629 days.

(21) Appl. No.: 11/042,041

(22) Filed: Jan. 25, 2005

(65) Prior Publication Data

US 2006/0165269 A1    Jul. 27, 2006

(51) Int. Cl.
*G06K 9/00* (2006.01)
(52) U.S. Cl. .................. 382/128; 382/115; 356/4.07
(58) Field of Classification Search ............... 382/100, 382/106, 108, 115, 116, 120, 123–126, 128, 382/168, 172, 181, 184, 191, 194, 199, 203, 382/219, 232, 256, 274–276, 305, 312, 316–321; 482/48, 47; 462/1; 356/4.07
See application file for complete search history.

(56) References Cited

U.S. PATENT DOCUMENTS

| | | | | | |
|---|---|---|---|---|---|
| 6,002,784 | A | * | 12/1999 | Sato | 382/124 |
| 6,002,787 | A | * | 12/1999 | Takhar et al. | 382/125 |
| 6,282,304 | B1 | * | 8/2001 | Novikov et al. | 382/125 |
| 6,996,259 | B2 | * | 2/2006 | Cannon et al. | 382/125 |
| 7,203,344 | B2 | * | 4/2007 | McClurg et al. | 382/115 |
| 7,272,247 | B2 | * | 9/2007 | Hamid | 382/124 |

* cited by examiner

*Primary Examiner*—Seyed Azarian
(74) *Attorney, Agent, or Firm*—Charles E. Baxley

(57) ABSTRACT

A dermatoglyph test system examines dermatoglyph of fingers, big toes and palms comprising at least an image capture device to capture images of testers' all fingers, big toes and palms dermatoglyph, a recognition unit to recognize the features of dermatoglyph and an output unit to output the features of the dermatoglyph in characters.

9 Claims, 6 Drawing Sheets

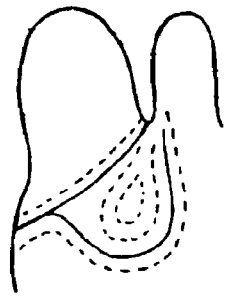
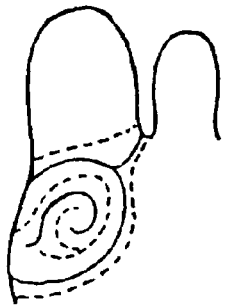
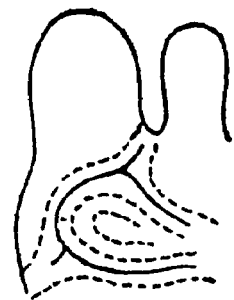
FIG.8
PRIOR ART
FIG.9
PRIOR ART
FIG.10
PRIOR ART
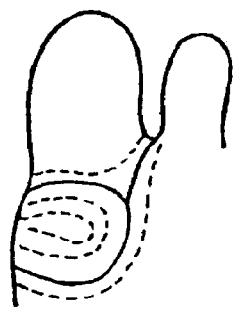
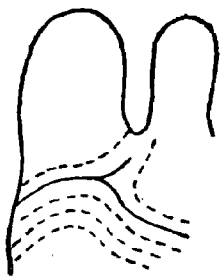
FIG.11
PRIOR ART
FIG.12
PRIOR ART
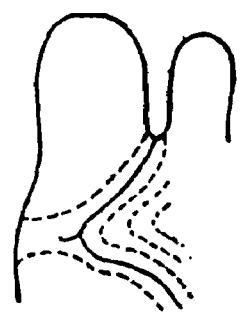
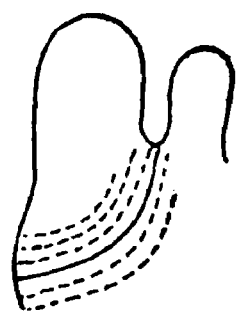
FIG.13
PRIOR ART
FIG.14
PRIOR ART

DERMATOGLYPH TEST SYSTEM

BACKGROUND OF THE INVENTION

I. Field of the Invention

This invention relates generally to a test system and, more specifically, to a dermatoglyph test system that tests skin ridge of human fingers, palms and thenars.

II. Description of the Prior Art

Heretofore, it is known that human skin comprises epidermis and derma. Derma forms many papillaries toward epidermis aligned in parallel, such protruding stripes are called ridge, many furrows are between two ridges, these ridges and furrows constitute human finger prints and palm prints.

The ridges and furrows of human skin develop from 13 years old and complete around 19 years old; once completed, they will not change for life; Marer in 1788 had the theory that no two persons have the same ridges and furrows.

In 1823, a Czech physiologist Phkinje published a thesis over ridges; he states the shapes of ridges are in Loop, Whorl and Arches.

In 1926, two American anatomist Cammis and Midlo reported peculiar dermatoglyph characters of Down Syndrome patients, 20 years later a French hereditist and cytologist Lejeuhca found that peculiar dermatoglyph have close relation with extraordinary chromosome.

At present time, dermatoglyph test became a very important clinical diagnosis method; further more a very effective test to be applied to public as a general examination and prediction.

Following describes the dermatoglyph characters of normal people:

The dermatoglyph shapes are in Loop, Whorls and Arches. The Loop, as shown in FIG. 1, is the dermatoglyph go from one side to another side with curve in between; the Whorls, as shown in FIG. 2, is the dermatoglyph bend from one side, curve upward then return to the origin, a triangle shape is under the top, the center is called Triadius; the Arches, as shown in FIG. 3, has two forks, besides that, a special character as Ridge count shown in FIG. 4 and FIG. 5, is to have a straight line from the center of the Loop or the Whorl to the Triadius then count the numbers of the dermatoglyph along this straight line. Since the Arches do not have the Triadius, the Arches have no Ridge count.

As shown in FIG. 6, palm prints are classified in five parts: nar area 10 beneath thumb; Hypothenar area 12 beneath little finger; interdigital area 11, 12, 13, 14; Triadius a, b, c and d are on the base of index, middle and ring fingers; line A, B, C and D are stretched out from each of the Triadius; Triadius t are on the center of base of palm. Besides these, an angle called ∠atd, as shown in FIG. 7, formed by Triadius a and Triadius d to Triadius t, this angle is measured to indicate the locations of Triadius, the angle of normal people is 41° and the angle of Down Syndrome patients is 64°.

The only dermatoglyph of the big toe of Thenar prints has sufficient research and clinical meaning up till now, as sown in FIG. 8 to FIG. 14, dermatoglyph of big toe can be categorized in 7 types: from FIG. 8 to FIG. 14, they are far-side Whorl, Loop, off-center Whorl, off Whorl, near-side Arches, side Arches and off side Arches.

SUMMARY OF THE INVENTION

It is therefore a primary object of the invention to provide a dermatoglyph test system that examines human finger pints, palm prints and big toe prints.

In order to achieve the objective set forth, a dermatoglyph test system in accordance with the present invention examines dermatoglyph of fingers, big toes and palms and comprises an image capture device to capture images of testers' all fingers, big toes and palms dermatoglyph;

a recognition unit to recognize the features of dermatoglyph;

an output unit to output the features of the dermatoglyph in characters.

BRIEF DESCRIPTION OF THE DRAWINGS

The accomplishment of the above-mentioned object of the present invention will become apparent from the following description and its accompanying drawings which disclose illustrative an embodiment of the present invention, and are as follows:

FIG. 8 is a perspective view of far-side Whorl of big toe dermatoglyph;

FIG. 9 is a perspective view of Loop of big toe dermatoglyph;

FIG. 10 is a perspective view of off-center Whorl of big toe dermatoglyph;

FIG. 11 is a perspective view of off Whorl of big toe dermatoglyph;

FIG. 12 is a perspective view of near-side Arches of big toe dermatoglyph;

FIG. 13 is a perspective view of side Arches of big toe dermatoglyph;

FIG. 14 is a perspective view of off side Arches of big toe dermatoglyph;

DESCRIPTION OF THE PREFERRED EMBODIMENT

The present invention carries out three dermatoglyph test processes: finger prints, big toe and palm prints.

Figure 1:
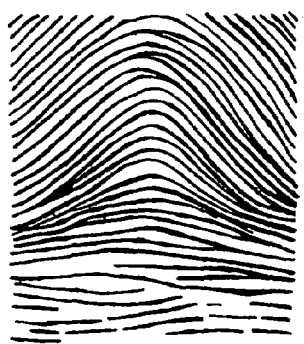
FIG. 1 is a perspective view of Arches dermatoglyph.
Figure 2:
FIG. 2 is a perspective view of Loop dermatoglyph.
Figure 3:
FIG. 3 is a perspective view of Whorl dermatoglyph.
Figure 4:
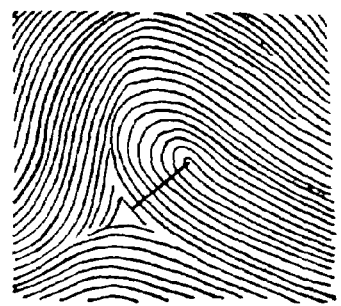
FIG. 4 is a perspective view of Ridge count.
Figure 5:
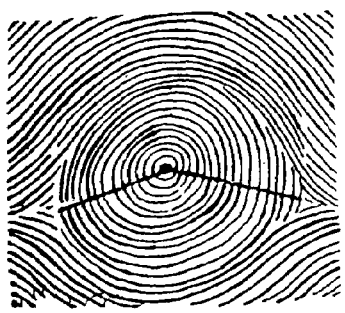
FIG. 5 is another perspective view of Ridge count.
Figure 6:
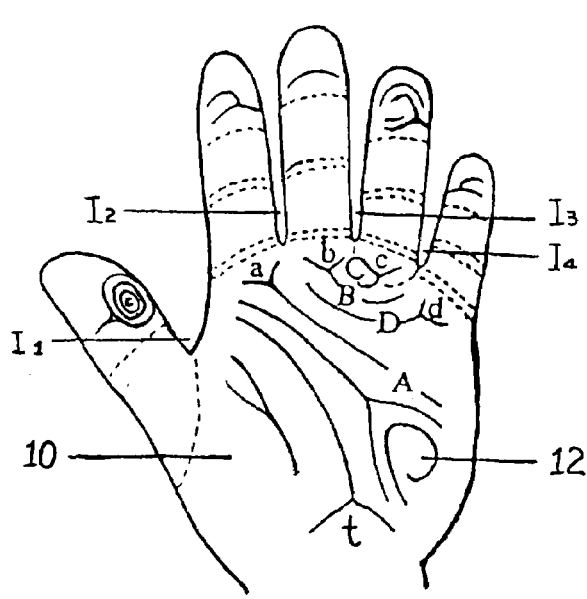
FIG. 6 is a perspective view of palm prints of normal people.
Figure 7:
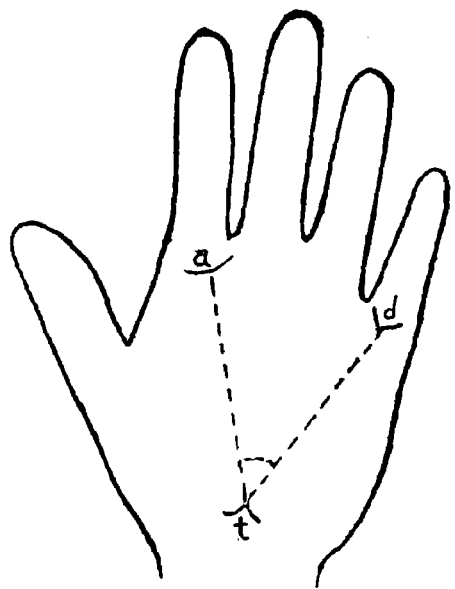
FIG. 7 is a perspective view of ∠atd of palm prints.
Figure 15:
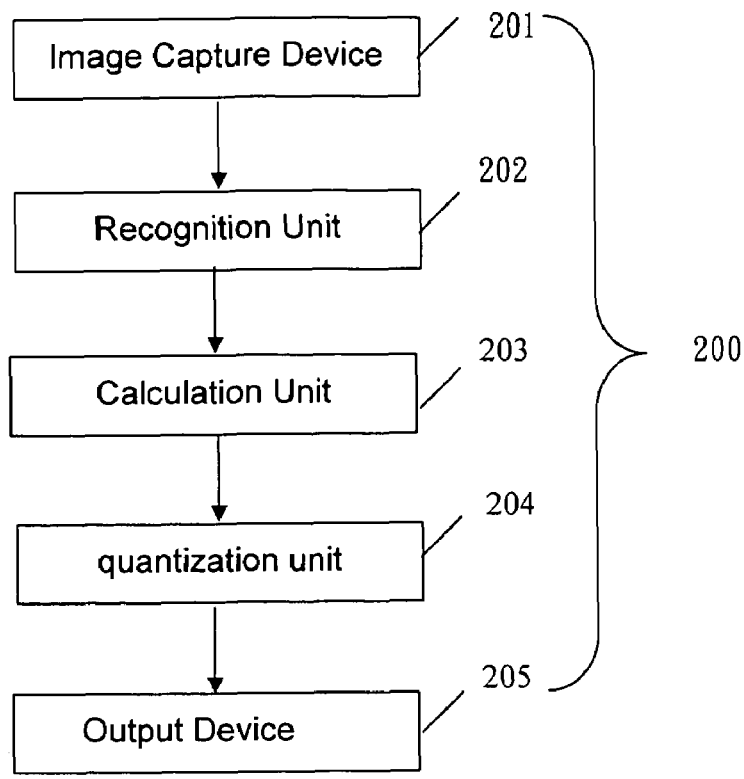
FIG. 15 is a flow chart of dermatoglyph tester of fingers of a further embodiment of the present invention.
Figure 16:
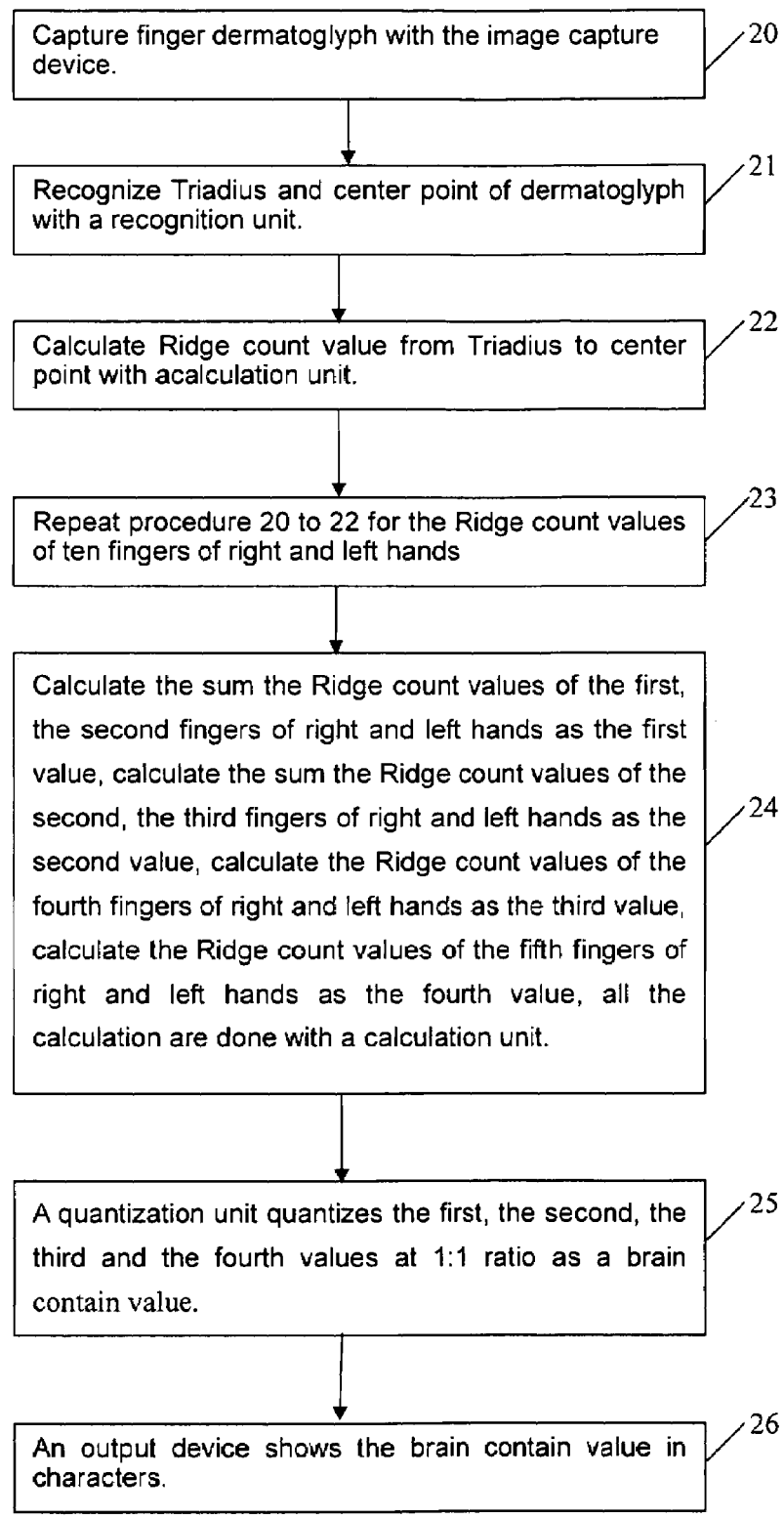
FIG. 16 is a flow chart of dermatoglyph tester of fingers of a further embodiment of the present invention.

As shown in FIG. 15 and FIG. 16, the finger prints test process 200 executes following procedures:

Procedure 20: capture finger dermatoglyph with the image capture device 201, such as scanner.

Procedure 21: recognize Triadius and center point of dermatoglyph with a recognition unit 202.

Procedure 22: calculate Ridge count value from Triadius to center point with the recognition unit 202.

Procedure 23: repeat procedure 20 to 22 for the Ridge count values of ten fingers of right and left hands.

Procedure 24: calculate the sum the Ridge count values of the first, the second fingers of right and left hands as the first value, calculate the sum the Ridge count values of the second, the third fingers of right and left hands as the second value, calculate the Ridge count values of the fourth fingers of right and left hands as the third value, calculate the Ridge count values of the fifth fingers of right and left hands as the fourth value, all the calculation are done with a calculation unit 203.

Procedure 25: a quantization unit 204 quantizes the first, the second, the third and the fourth values at 1:1 ratio as a brain contain value.

Procedure 26: an output device 205 shows the brain contain value in characters.

The brain contain value is an indicator of learning priority. Human brain further contains frontal lobe, cerebrum, temporal lobe and occipital lobe; frontal lobe is in charge of exercise of the extremities, sleeping, oral expression, thinking, judgment and planning; cerebrum is in charge of perception of the extremities, oral function, space visual function; temporal lobe is in charge of voice function, language recognition, memory and emotion; and occipital lobe is in charge of visual perception, visual recognition; based on relation of the defined brain zone and Ridge count values, the test results can judge if of the brain zones is superior. The corresponding relation of the Ridge count values and the brain zones is following: frontal lobe corresponds to the sum of the first, the second Ride count value of the right and left hands; cerebrum corresponds to the sum of the second, the third Ride count value of the right and left hands; temporal lobe corresponds to the sum of the fourth Ride count value of the right and left hands; and occipital lobe corresponds to the sum of the fifth Ride count value of the right and left hands. If the sum of the first, the second Ride count value of the right and left hands is the largest of the frontal lobe, cerebrum, temporal lobe and occipital lobe value, that means frontal lobe is the most superior, the communication, expression, thinking, judgment, creation and planning is superior.

Figure 17:
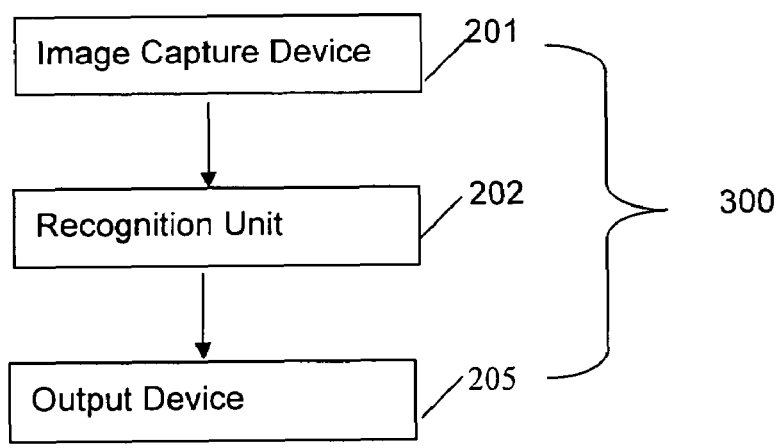
FIG. 17 is a flow chart of dermatoglyph tester of big toe of a further embodiment of the present invention.
Figure 18:
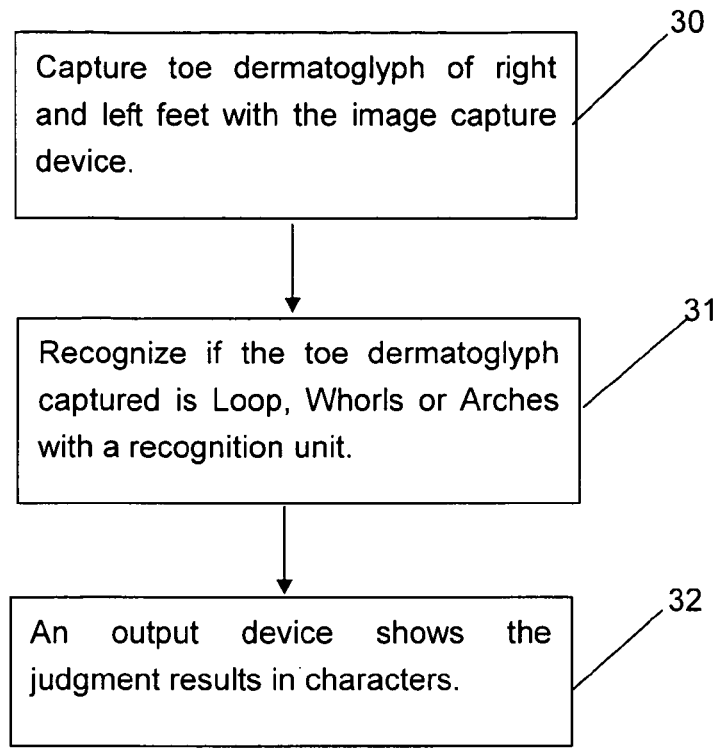
FIG. 18 is a flow chart of dermatoglyph tester of big toe of a further embodiment of the present invention.

As shown in FIG. 17 and FIG. 18, the big toe test process 300 executes following procedures:

Procedure 30: capture toe dermatoglyph of right and left feet with the image capture device 201.

Procedure 31: recognize if the toe dermatoglyph captured is Loop, Whorls or Arches with a recognition unit 202.

Procedure 32: an output device 205 shows the judgment results in characters.

The judgment results is one of the heredity judgment factors; if the tester's left toe dermatoglyph is Whorls and left toe dermatoglyph is Loop, or left toe dermatoglyph is Loop, right toe dermatoglyph is Whorls, or both toe dermatoglyph are Whorls, or both toe dermatoglyph are Loop, the heredity gene is healthy; when left toe dermatoglyph is Loop, right toe dermatoglyph is Loop and one of them has a mark, this tester might have allergy problem or the family heredity gene problem; when left toe dermatoglyph is Loop, right toe dermatoglyph is Loop and too many spots, strong keen color; when both toes dermatoglyph are Arches, the tester might have specific heredity with Down Syndrome or learning problems; when both toe dermatoglyph are in other shapes, the tester might have allergy or other gland heredity issues.

Figure 19:
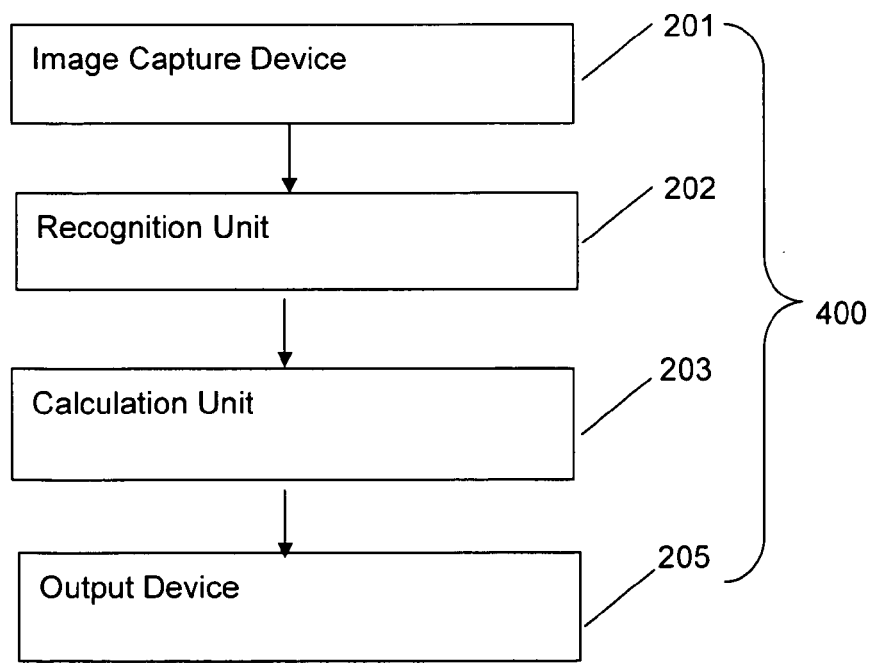
FIG. 19 is a flow chart of dermatoglyph tester of palm of a further embodiment of the present invention.
Figure 20:
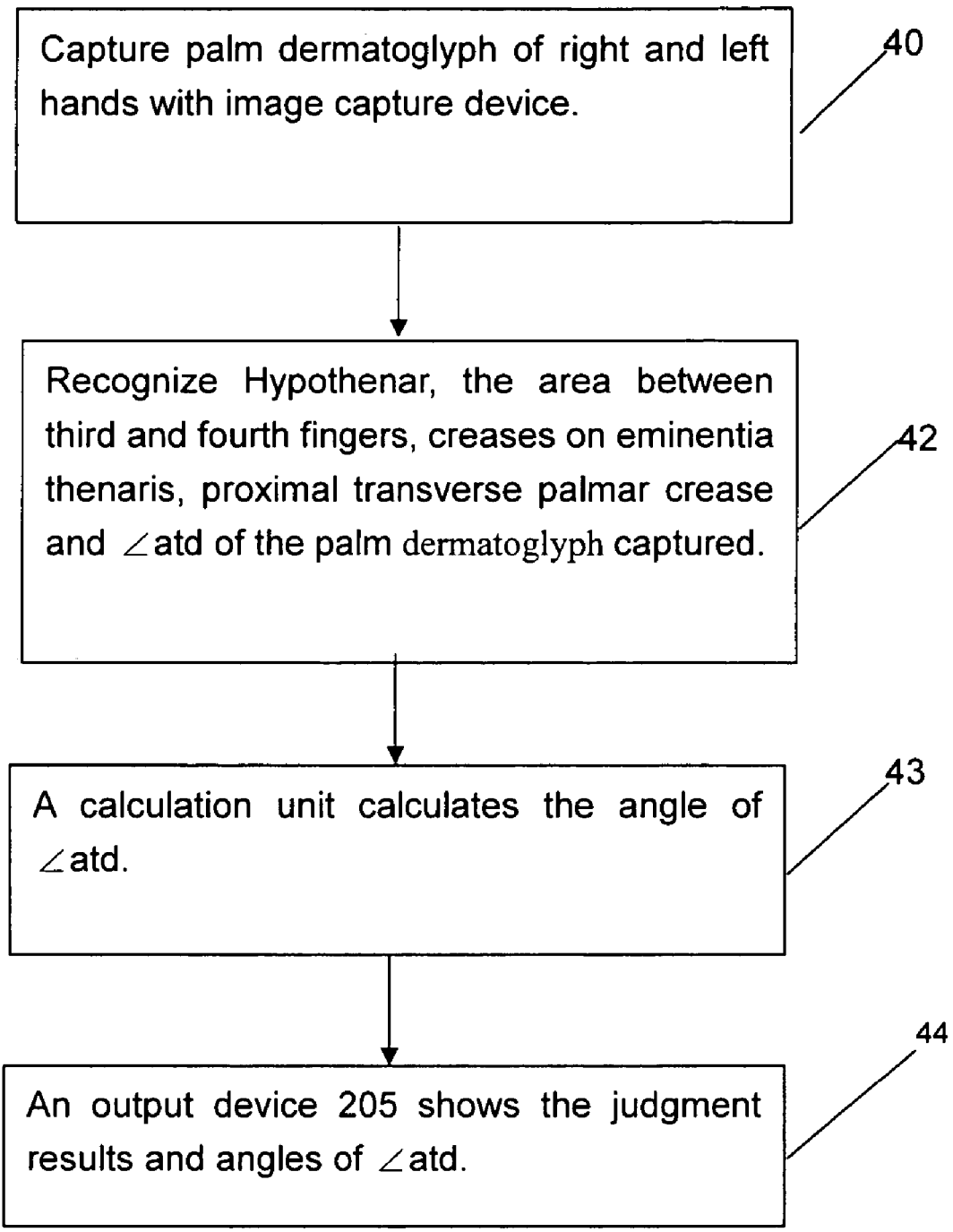
FIG. 20 is a flow chart of dermatoglyph tester of palm of a further embodiment of the present invention.

As shown in FIG. 19 and FIG. 20, the palm prints test process 400 executes following procedures:

Procedure 40: capture palm dermatoglyph of right and left hands with image capture device 201.

Procedure 42: recognize Hypothenar, the area between third and fourth fingers, creases on eminentia thenaris, proximal transverse palmar crease and ∠atd of the palm dermatoglyph captured.

Procedure 43: a calculation unit 203 calculates the angle of ∠atd.

Procedure 44: an output device 205 shows the judgment results and angles of ∠atd.

The judgment results is one of the heredity judgment factors; if the tester's right and left palm prints are both hypothenar, the test might have allergy; when tester's right and left palms are third and fourth fingers areas or right and left palms are third and fourth fingers areas and one of them has hook, the tester has strong allergy. If tester's left hand has creases on eminentia thenaris with a hook, this tester has week gland heredity. If tester's left hand has proximal transverse palmar crease or right hand has proximal transverse palmar crease, or left hand has proximal transverse palmar crease with a hook, or right hand has proximal transverse palmar crease with a hook, the tester is dominant heredity. When ∠atd<=39 degree, the tester's learning pace is fast and can do delicate movement, when ∠atd<=50 degree, the tester's learning pace is slow and has awkward movement.

While a preferred embodiment of the invention has been shown and described in detail, it will be readily understood and appreciated that numerous omissions, changes and additions may be made without departing from the spirit and scope of the invention.

What is claimed is:

1. A dermatoglyph test system examines three dermatoglyph test processes: finger prints, big toe and palm prints comprising:
    an image capture device to capture tester's finger prints, big toe and palm prints;
    a recognition unit to recognize dermatoglyphs' features;
    an output device to show dermatoglyphs' features in characters wherein said dermatoglyphs' features are Triadius and center points of finger prints wherein a calculation unit calculates the Ridges count values from Triadius to center points wherein said calculation unit calculates the sum the Ridge count values of the first, the second fingers of right and left hands as the first value, the sum the Ridge count values of the second, the third fingers of right and left hands as the second value, Ridge count values of the fourth fingers of right and left hands as the third value, the Ridge count values of the fifth fingers of right and left hands as the fourth value.

2. The dermatoglyph test system recited in claim 1, wherein a quantization unit quantizes said first, second, third and fourth values as a brain contain value.

3. The dermatoglyph test system recited in claim 2, wherein said brain contain values are at 1:1 ratio.

4. The dermatoglyph test system recited in claim 2, wherein said output unit output the brain contain values in characters.

5. A dermatoglyph test system examines three dermatoglyph test process: finger prints, big toe and palm prints comprising:
    an image capture device to capture tester's finger prints, big toe and palm prints;
    a recognition unit to recognize dermatoglyphs' features;
    an output device to show dermatoglyphs' features in characters wherein palm dermatoglyph are Hypothenar, the area between third and fourth fingers, creases an eminentia thenaris, proximal transverse palmar crease and ∠atd wherein a calculation unit calculates the angle ∠atd.

6. The dermatoglyph text system recited in claim 5, wherein said output device output the dermatoglyph features in characters and the angles of ∠atd.

7. A dermatoglyph test method is done in a hardware system comprising following procedures;
- a) capture tester's finger dermatoglyph;
- b) recognize Triadius and center point of finger print;
- c) calculate the Ridge count values from Triadius to center points;
- d) repeat procedure a), b) and c) for Ridge count values of ten fingers of right and left hands;
- e) calculate the sum the Ridge count values of the first, the second fingers of right and left hands as the first value, the sum the Ridge count values of the second, the third fingers of right and left hands as the second value, Ridge count values of the fourth fingers of right and left hands as the third value, the Ridge count values of the fifth fingers of right and left hands as the fourth value;
- f) output said first, second, third and fourth values wherein said first, second, third and fourth values in said procedure e) are quantized at a certain ration as a brain contain value.

8. The dermatoglyph test system recited in claim 7, wherein said brain contain values are at 1:1 ratio.

9. The dermatoglyph test system recited in claim 7, wherein said procedure f) outputs said brain contain value.

\* \* \* \* \*